United States Patent [19]

Pyka et al.

[11] Patent Number: 5,002,563
[45] Date of Patent: Mar. 26, 1991

[54] SUTURES UTILIZING SHAPE MEMORY ALLOYS

[75] Inventors: Walter R. Pyka, Redwood City; Hank C. K. Wuh, Palo Alto; Lee M. Middleman, Portola Valley, all of Calif.

[73] Assignee: Raychem Corporation, Menlo Park, Calif.

[21] Appl. No.: 483,596

[22] Filed: Feb. 22, 1990

[51] Int. Cl.$^5$ .................................................. A61B 17/00
[52] U.S. Cl. ..................................... 606/222; 606/223; 606/78
[58] Field of Search .......................... 606/222, 223, 78

[56] References Cited

U.S. PATENT DOCUMENTS

| | | | |
|---|---|---|---|
| 3,620,212 | 11/1971 | Fannon et al. | 128/839 |
| 3,786,806 | 1/1974 | Johnson et al. | 606/78 |
| 3,890,977 | 6/1975 | Wilson | 604/281 |
| 4,170,990 | 10/1979 | Baumgart | 606/78 |
| 4,485,816 | 12/1984 | Krumme | 606/219 |
| 4,665,906 | 5/1987 | Jervis | 606/78 |
| 4,899,744 | 2/1990 | Fujitsuka et al. | 606/153 |
| 4,926,860 | 5/1990 | Stice et al. | 606/144 |

Primary Examiner—Randall L. Green
Assistant Examiner—Gary Jackson
Attorney, Agent, or Firm—Edith A. Rice; Herbert G. Burkard

[57] ABSTRACT

A suture and a suturing method are set forth for suturing a wound in the tissue of a patient and defined by tissue edges. The suture comprises an alloy member having a first end portion, a second end portion, and a first undeformed shape. It is deformable into a second deformed shape. The member has the property of recovering from its second shape towards its first shape upon the second shape being subjected to specified conditions. The first shape is a suturing loop adapted to draw and hold the tissue edges defining the wound together. The second shape is adapted to allow the member to be drawn through the tissue in position for the loop to form. The method comprises inserting such a member while it is in its second shape into position for it to assume its first suturing loop shape and subjecting it to conditions which cause it to recover towards its first shape.

49 Claims, 6 Drawing Sheets

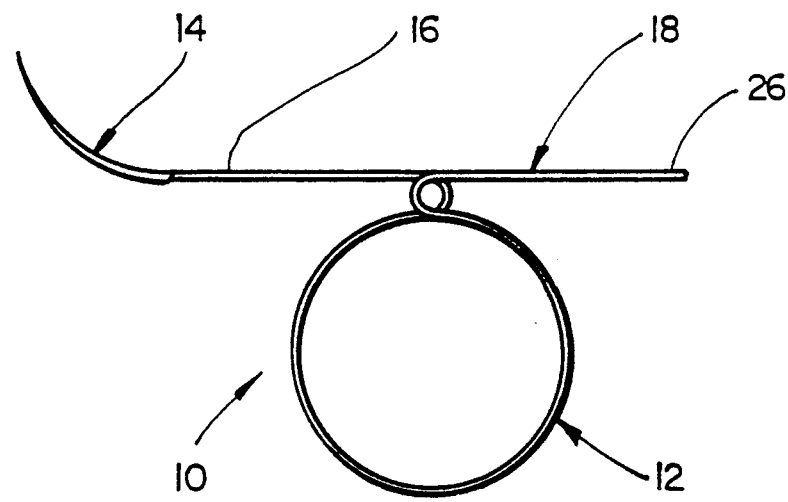
FIG_1
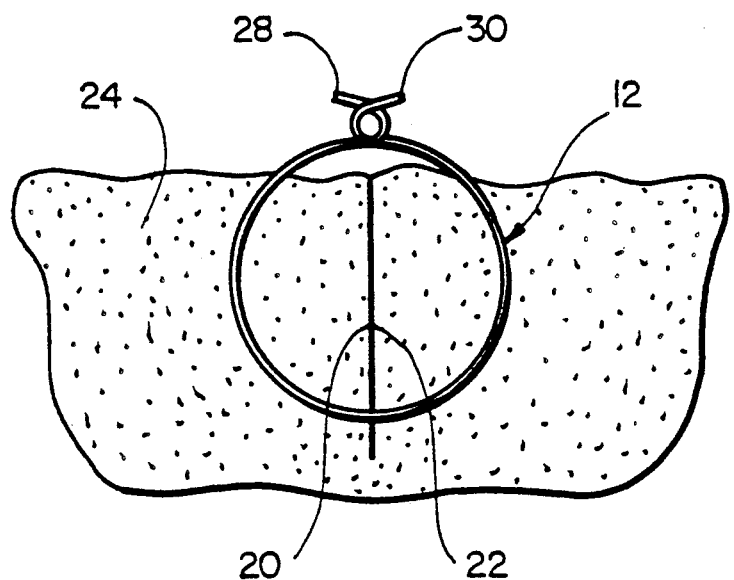
FIG_2

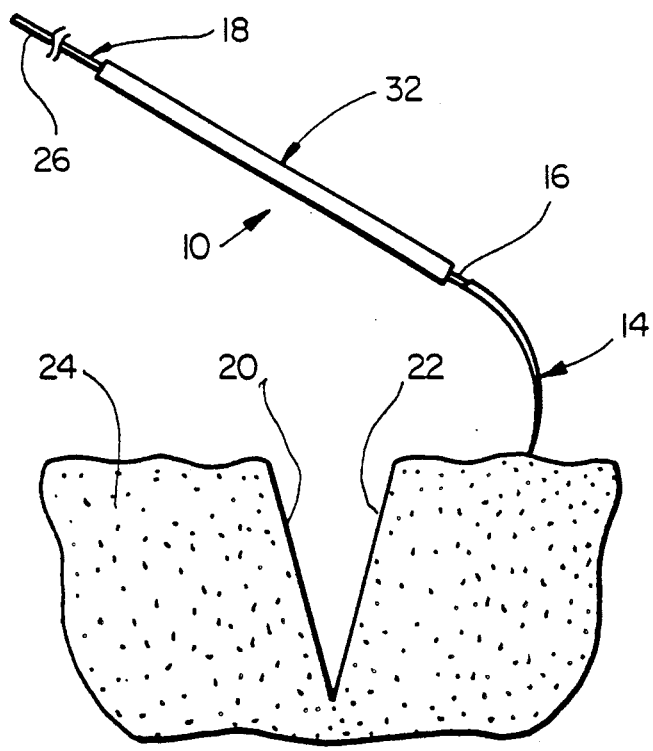
FIG_3
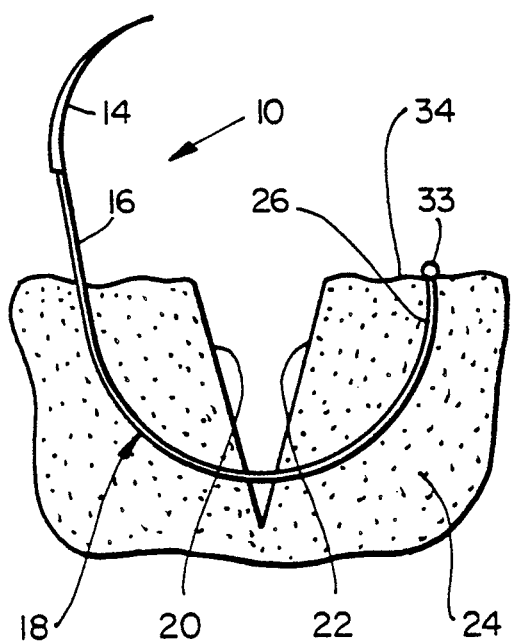
FIG_4A
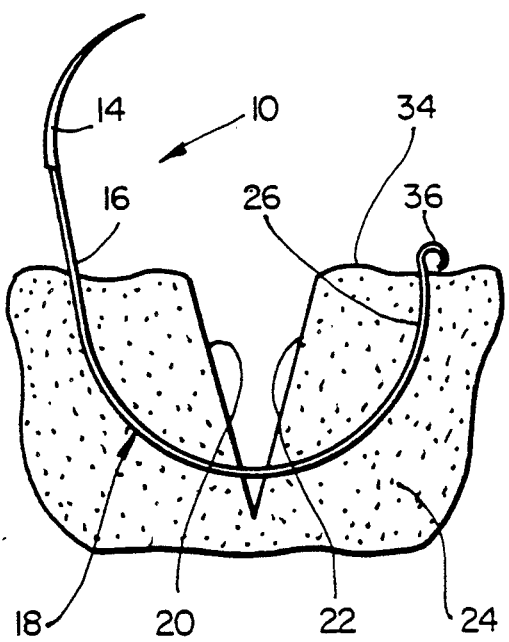
FIG_4B

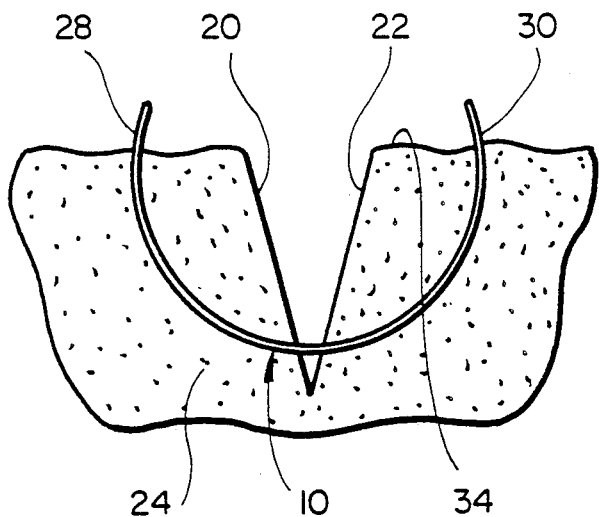
FIG_5A
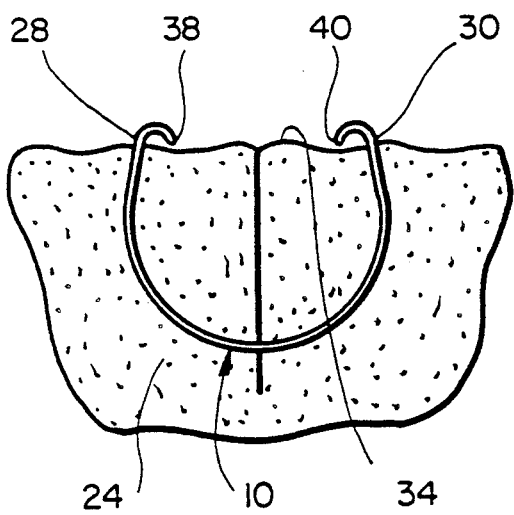
FIG_5B1
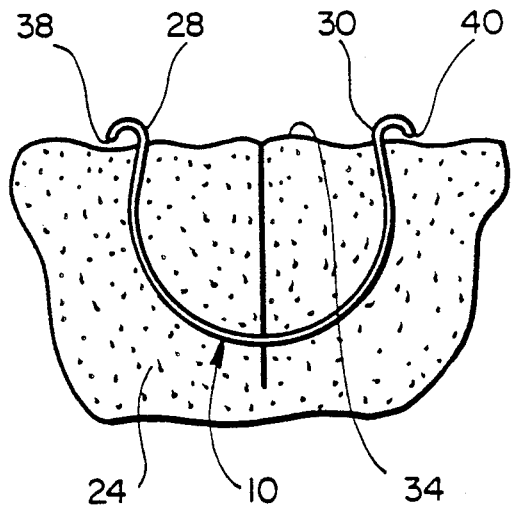
FIG_5B2

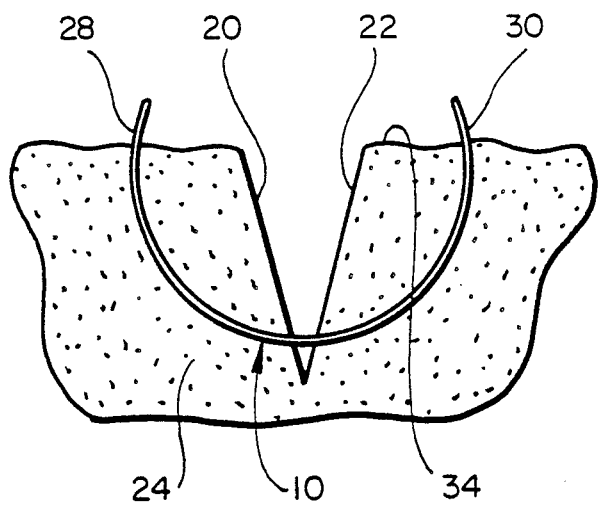
FIG_6A
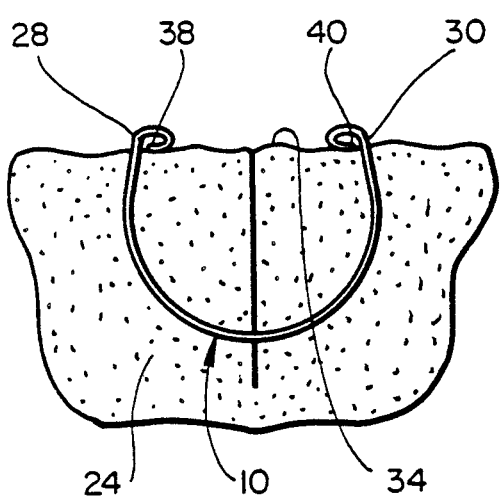
FIG_6B1
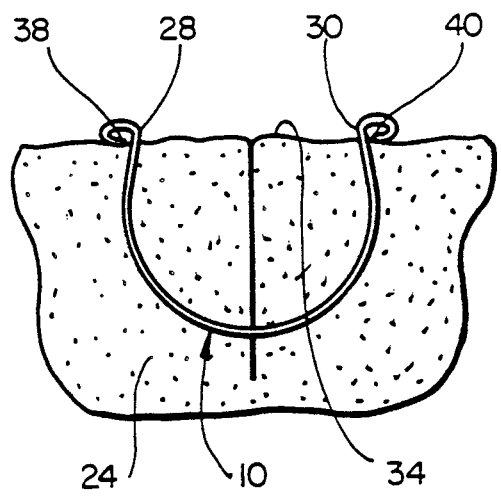
FIG_6B2

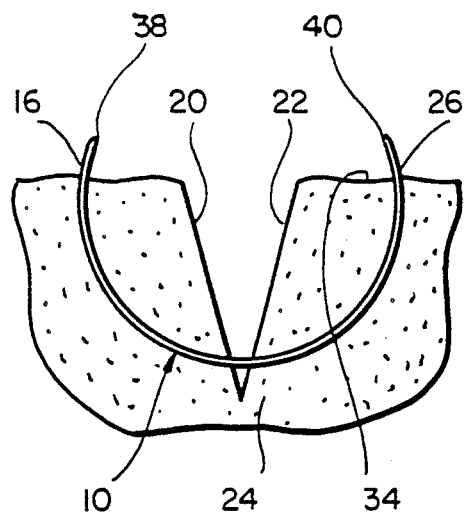
FIG_7A
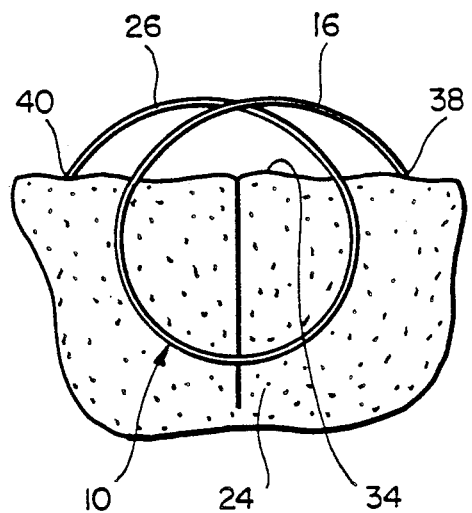
FIG_7B1
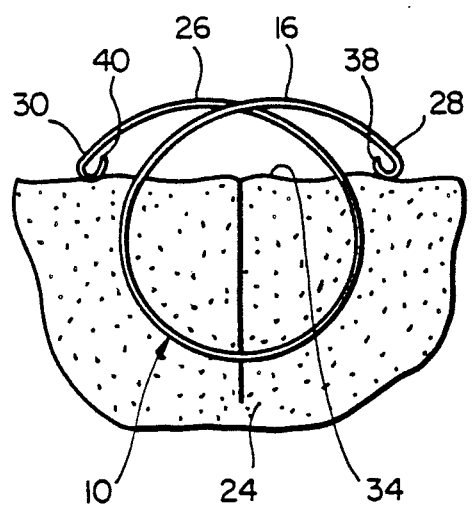
FIG_7B2
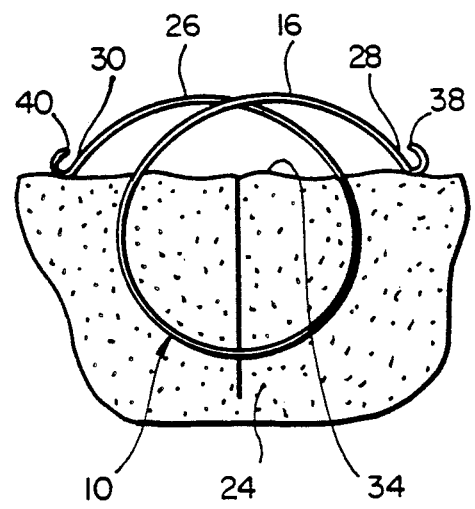
FIG_7B3

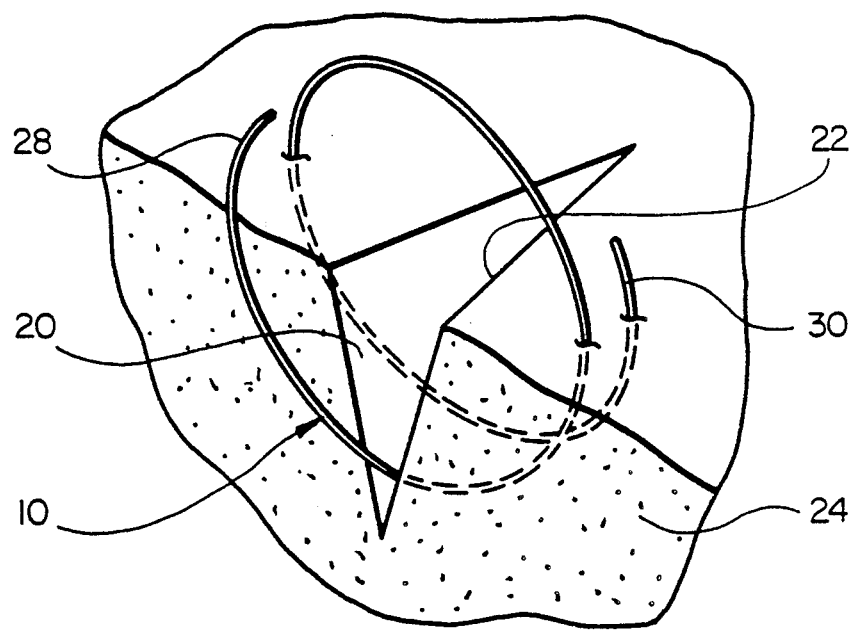
FIG_8A
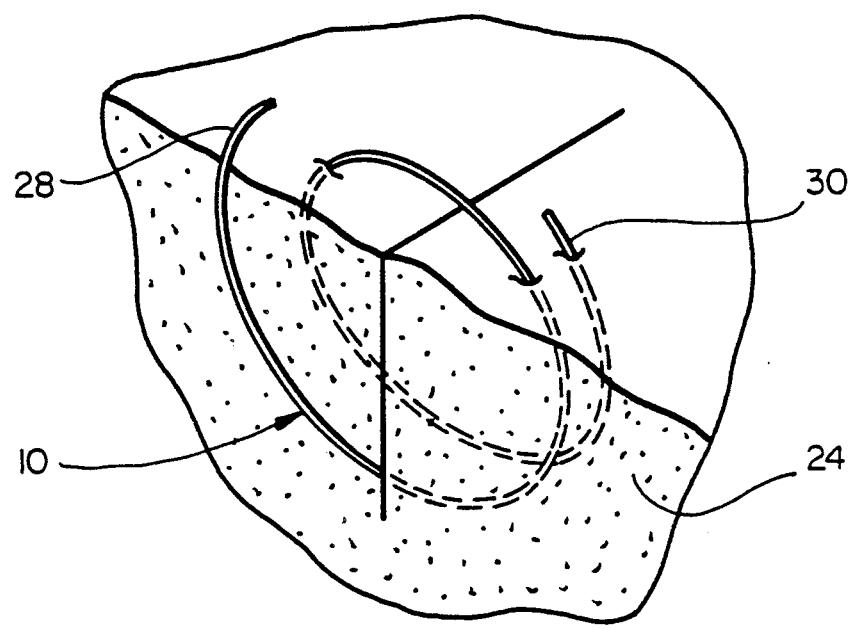
FIG_8B

SUTURES UTILIZING SHAPE MEMORY ALLOYS

TECHNICAL FIELD

The invention relates to surgical sutures which utilize shape memory alloys.

BACKGROUND OF THE INVENTION

Alloys which possess shape memory are well known. Articles made of such materials can be deformed from an original undeformed configuration to a second deformed configuration. Such articles revert to the undeformed configuration under specified conditions. They are said to have shape memory. One set of conditions which will enable a deformed configuration of an article having shape memory to recover towards its undeformed configuration or shape is the application of heat alone. In such an instance the material is spoken of as having an original heat-stable configuration and a second, heat-unstable configuration. The alloy is formed into the heat-unstable configuration at a temperature where it is in a predominantly martensitic phase. Upon application of heat, the article made of such a material can be caused to revert or to attempt to recover from its heat-unstable configuration towards its original heat-stable configuration, i.e., it "remembers" its original shape.

Among metallic alloys the ability to possess shape memory is the result of the fact that the alloy undergoes a reversible transformation from a predominantly austenitic state to a predominantly martensitic state with a decrease in temperature. This transformation is sometimes referred to as a thermoelastic martensitic transformation. An article made from such an alloy is easily deformed from its original configuration to a new configuration when cooled below the temperature at which the alloy is transformed from a predominantly austenitic state to a predominantly martensitic state. The temperature at which this transformation begins is usually referred to as $M_S$ and the temperature at which it finishes is usually referred to as $M_f$. When an article thus deformed is warmed to the temperature at which the alloy starts to revert back to its austenitic state, referred to as $A_S$ ($A_f$ being the temperature at which the reversion is complete), the deformed object will begin to return to its original configuration. Many shape memory alloys (SMAs) are known to display stress-induced martensite (SIM). When a SMA sample exhibiting such SIM is stressed at a temperature above $M_S$ (so that the austenitic state is initially stable), but below $M_d$ (the maximum temperature at which martensite formation can occur even under stress), it first deforms elastically and then, at a critical stress, begins to transform by the formation of SIM. Depending on whether the temperature is above or below $A_S$, the behavior when the deforming stress is released differs. If the temperature is below $A_S$, the SIM is stable; but if the temperature is above $A_S$, the martensite is unstable and transforms back to austenite, with the sample returning (or attempting to return) to its original shape. The effect is seen in almost all alloys which exhibit a thermoelastic martensitic transformation, along with the thermal shape memory effect. However, the extent of the temperature range for which SIM is seen, and the stress and strain ranges for the effect vary greatly with the alloy.

Various proposals have been made to employ shape memory alloys in the medical field. For example, U.S. Pat. No. 3,620,212 to Fannon et al. proposed the use of a SMA intrauterine contraceptive device; U.S. Pat. No. 3,786,806 to Johnson et al. proposes the use of a SMA bone plate; U.S. Pat. No. 3,890,977 to Wilson proposes the use of a SMA element to bend a catheter or cannula; U.S. Pat. No. 4,485,816 to Krumme, discloses use of a shape-memory surgical staple for use in holding the edges of a wound together while it heals; U.S. Pat. No. 4,170,990 to Baumgart shows the use of SMA's for medical purposes such as wires to correct scoliosis, disk clamps and intermedullary rods. Also, U.S. Pat. No. 4,665,906 to Jervis discloses medical devices which make use of the pseudoelastic (SIM) properties of such shape memory alloys.

These medical SMA devices rely on the property of shape memory, thermal or stress relieved, to achieve the desired effects. That is to say, they rely on the fact that when a SMA element is cooled to its martensitic state and is subsequently deformed, or when stress is applied which is causing a portion of the SMA to be in its martensitic form, it will retain its new shape; but when it is warmed to its austenitic state or the stress is relieved, as the case may be, the element recovers towards its original shape.

There are currently three different techniques used for holding the edges of a wound together while it heals. The oldest and most widely used method relies on the use of flexible threads which are passed through the apposing tissue edges and then tied. Such threads can be made of silk or of a synthetic polymeric material. Some such threads must be removed by the physician after healing has occurred while others will gradually be absorbed by the body. Another method relies on metal staples that are placed across the apposing tissue edges and then bent further inwardly to hold the wound edges together and prevent the staple from falling out. The final method relies on bands or strips which are placed across the wound with the bands or strips being held to the surface of the skin by an adhesive backing, by staples, or by sutures.

The metal staples and the bands or strips generally provide only surface closing of the wound and do not adequately hold the more deeply buried portions of the edge of the wound together.

Only sutures provide the important capability of holding together the more deeply buried portions of the edges of a wound. Such a capability is quite important since if the deep portion of a wound is not held together body fluids can accumulate and infection can occur in a region where the body's defenses cannot respond. And, the flexible sutures currently used, because of the fact that they are tied in place, provide a shear force which acts from deep in the wound to the surface of the wound as well as a force which tends to force the edges of the wound together. This shear force is not desirable in that it may interfere with proper alignment of the wound edges since it can cause the edges of the wound to pucker or bow apart. As a result, it is necessary to use two or more layers of sutures, one layer buried below the other, to adequately close a deep wound. Also, the skill of the individual surgeon determines how well currently flexible sutures will hold a wound together. And, it is difficult and time consuming to properly tie each of a series of successive sutures in a wound so as to provide the best possible closure of the wound.

The present invention is directed to overcoming one or more of the problems as set forth above.

DISCLOSURE OF THE INVENTION

In accordance with one embodiment of the present invention, a suture is set forth for suturing a wound in the tissue of a patient (human or animal) and defined by tissue edges. The suture comprises an alloy member having a first end portion, a second end portion, and a first undeformed shape. It is deformable into a second deformed shape. The member in its second shape has the property of recovering towards the first shape upon being subjected to specified conditions. The first shape is a suturing loop adapted to draw and hold the tissue edges defining the wound together. The second shape is adapted to allow the first end of the member to be drawn through the tissue in position such that on recovery of the member towards the first shape the tissue edges are urged together.

In accordance with another embodiment of the present invention, a method of suturing a wound in the tissue of a patient and defined by tissue edges is set forth. The method comprises inserting a member as set forth above while in its second shape through the tissue adjacent the tissue edges defining the wound and into position for the member to recover towards its first shape. The member is subjected to conditions which cause it to recover towards its first suturing loop shape whereby it draws and holds the tissue edges of the wound together.

Shape memory alloy sutures in accordance with the present invention can overcome all of the problems of the prior art as discussed above. They differ from staples and from bands or strips in that they are useful for holding the edges of deep wounds together. They differ from conventional sutures in that they do not require tieing off and they do not cause any shear force between the depths of the wound and the surface. Furthermore, such sutures can generally be readily removed following sufficient healing of the wound. Such sutures, when placed across the wound, help to draw the tissue edges abuttingly together and keep them apposed until the wound is healed. They can close thick layers of tissue utilizing a single set of sutures as opposed to the use of multiple layers of the prior art sutures being required to close a thick layer of tissue. And, tying is not required to secure wound closure.

Utilizing conventional sutures, it is normally necessary to have multiple layers of such sutures, starting at the bottom of the wound and working upwardly toward the tissue surface. This requires considerably more operating time. In addition, the sutures of the present invention do not require tying which also saves considerable time in wound closure. The time saved decreases the risk of surgery to the patient since the operating time is shortened which decreases the risks of anesthesia and the wound is open for a shorter period of time, which decreases the risk of infection. Also, the shorter wound closing time can result in cost savings to the patient since the total time which the patient spends in the operating room is thereby decreased.

BRIEF DESCRIPTION OF THE DRAWINGS

The invention will be better understood by reference to the Figures of the drawings wherein like numbers denote like parts throughout and wherein:

FIG. 1 illustrates a suture in accordance with the present invention in its loop form and with a needle attached;

FIG. 2 illustrates a suture in accordance with the present invention in its loop form in final position across a wound;

FIG. 3 illustrates a suture in accordance with the present invention along with an insertion aid;

FIG. 4a illustrates an embodiment of the suture in accordance with the present invention;

FIG. 4b illustrates another embodiment of the suture in accordance with the present invention;

FIG. 5 illustrates a suture in accordance with the present invention in its deformed form and further illustrates two different undeformed shapes which it may assume;

FIG. 6 illustrates an embodiment of a suture in accordance with the present invention in its deformed form and further illustrates two different undeformed shapes it may assume;

FIG. 7 illustrates an embodiment of a suture in accordance with the present invention in its deformed form and further illustrates three different undeformed shapes it may assume; and FIG. 8 illustrates still another embodiment of a suture in accordance with the present invention.

BEST MODE FOR CARRYING OUT INVENTION

The present invention, in its embodiments, makes use of the property of shape memory to achieve its desired effect. The conditions which cause the SMA devices of the present invention to be shifted from their deformed shape to their undeformed shape may be either the temperature effect, that is, heating the SMA to the temperature at which the martensitic-to-austenitic conversion occurs, or the relaxation of stress which is maintaining a portion of the alloy in its martensitic state whereby it reverts to a more austenitic state. A combination of these effects can also be utilized. Potentially all of the physical embodiments of the suture of the present invention which will be described in following can make use of either of these two different shape memory characteristics of shape memory alloys.

When a SMA is used it will generally be a nickel-titanium based alloy which may include additional elements which might affect the yield strength that is available from the alloy or the temperature at which particular desired pseudoelastic or temperature shape transformation characteristics are obtained. For example, the alloy may be a binary alloy consisting essentially of nickel and titanium, for example, 50.8 atomic percent nickel and 49.2 atomic percent titanium, or it may include a quantity of a third element such as vanadium, chromium or iron. Alloys consisting essentially of nickel, titanium and vanadium, such as disclosed in U.S. Pat. No. 4,505,767, work quite well for some applications since they can exhibit non-linear pseudoelastic properties at or around body temperatures. Copper based alloys may also be used, for example, alloys consisting essentially of copper, aluminum and nickel; copper, aluminum and zinc; and copper and zinc.

FIG. 1 illustrates one embodiment of a suture 10 in accordance with the present invention. The suture 10 illustrated in FIG. 1 is made of a shape memory alloy as described above. It is in its predominantly austenitic state which, in accordance with the present invention, comprises a loop 12. The suture 10 shown in FIG. 1 includes a needle 14 attached to or formed out of a first end portion 16 of a member 18 which is in the form of an alloy strip or wire. The alloy strip or wire can have any convenient cross-sectional shape and dimension and can have different cross-sectional shapes and dimensions along different portions of its length. The needle 14 can have any convenient d style, or radius of curvature, but its diameter is generally greater than or equal to the greatest cross-sectional diameter of the member 18 so that the member 18 can follow it through tissue.

The needle 14 can be swaged onto, crimped, welded, soldered or otherwise attached to the first end portion 16 of the member 18. The needle 14 can be attached to the first end portion 16 of the member 18 such that it can readily be detached therefrom with a sudden tug. Alternatively, the member 18 can itself be sharpened (and possibly stiffened) to obviate the need for the needle 14. If desired, the needle 14 can be attached to the member 18 by including an eye (not illustrated) on the needle 14 and then passing the first end portion 16 of the member 18 through the eye.

As stated, the member 16 may take advantage of either the pseudoelastic property of the shape memory alloy, or the temperature-induced shape memory change of the SMA, or of a combination of these two properties. For a pseudoelastic suture, the shape shown in FIG. 1 is the undeformed loop configuration. A member 18 having this configuration can be readily manually straightened with part of the austenitic phase being converted to martensitic phase so long as the stress is maintained. As soon as the deforming force (stress) is removed, the suture 10 then returns pseudoelastically to its parent or loop configuration as illustrated in FIG. 1 with part of the martensitic phase converting back to austenitic phase.

In use, the suture 10 of FIG. 1 is placed under sufficient stress to deform it into a deformed state which is straight enough for it to be threaded through the tissue 24 and is conventionally threaded through the tissue 24 surrounding the wound thereby bringing the edges 20 and 22 of the wound into apposition as illustrated in FIG. 2. As the stress is removed, the suture 10 undergoes a martensitic to austenitic conversion and forms the loop 12 by springing back due to its pseudoelastic nature to the same shape shown in FIG. 1. Indeed the conversion can occur as the suture 10 is inserted. The tissue 24 itself may serve to straighten the suture 10 as it is threaded therethrough. It should be noted that while the loop 12 is shown as being circular in shape, and while such is generally contemplated, other shapes are also usable, for example elliptical shapes, rectangular shapes, and the like. Note that the loop 12 is fixed in final shape whereby it can be designed so as not to provide a deleterious shear force while providing the desired abutting force to appose the wound edges 20 and 22. Since the suture 10 is pseudoelastic, it is easily deformable and the member 18 will temporarily, due to the resistance of the tissue to formation of the loop 12, stay sufficiently in its martensitic state to allow it to be properly threaded into place. Accordingly, the suture 18 slides easily through the tissue 24.

The needle 14 is then cut off or otherwise removed, generally along with part of the first end portion 16, and in certain embodiments, part of the second end portion 26, of the member 18 thereby leaving end segments 28 and 30 as illustrated in FIG. 2. The loop 12 forms and serves to appose the tissue edges 20 and 22. The end segments 28 and 30 assume their curved parent (undeformed) configurations. End segments 28 and 30 can be interlocked manually or with instruments, if desired, to secure the wound closure. However, such interlocking is not essential and other embodiments of the invention do not necessarily utilize such interlocking.

When the wound is healed sufficiently, the suture 10 can be removed by cutting off one or both of end segments 28 and 30 and then sliding the remainder of the suture 10 out of the tissue 24.

FIG. 3 illustrates an embodiment of the present invention wherein a stiff sleeve 32 serves to retain the suture 10 in a relatively longitudinally extending shape. In the embodiment shown in FIG. 3, the sleeve 32 can be used to directly drive the needle 14 through the tissue 24. The sleeve 32 can also have a sharpened distal end and can be used to push the member 18 through the tissue 24. For a pseudoelastic suture 10, the needle 14 should be held by the sleeve 32 so that it does not rotate relative to the sleeve 32. Furthermore, the longitudinal axis of the portion of the needle 14 which joins the suture 10 should not flex significantly relative to the longitudinal axis of the sleeve 32. Once the needle 14 has been driven appropriately through the tissue 24, the suture 10 can be advanced further with the help of an instrument such as a conventional needle holder (not shown) and the sleeve 32 can simply be slipped off of the second end portion 26 of the member 18.

The embodiment of FIG. 1 can also illustrate a suture 10 which is converted from its predominantly martensitic state to its predominantly austenitic state by being heated to the temperature at which such a conversion occurs. In FIG. 1, the suture 10 is illustrated, under this interpretation, in its predominantly austenitic or undeformed state with the loop 12 in the position in which it would be used if inserted into tissue. Such a suture 10 can be cooled, for example by immersing it in a cold medium such as cold water, cold saline, liquid nitrogen, ice, liquid carbon dioxide, or the like, or by refrigerating it to a desired temperature prior to use. Once the suture 10 is cooled, it is then physically straightened and is driven through the tissue 24 as illustrated, for example, in FIG. 4a. The relatively malleable state of the suture 10, due to its relatively cool temperature, allows it to pass through the tissue 24 easily. Once the suture 10 is in position across the wound, the needle 14 and possibly a part of end portion 16 is cut off and removed. The remainder of the suture 10 allowed to warm to body temperature. Alternatively, the suture 10 may be additionally heated by placing a warm object against it, by immersing it and the wound in a warm medium, or by passing a current through it to create heat by electrical resistance. In any event, the increased temperature of the suture 10 causes the SMA to revert towards its predominantly austenitic parent state and thereby causes the suture 10 to reassume the configuration shown in FIG. 2 with resulting reformation of the loop 12. Some recovery toward the predominantly austenitic state can occur as the suture 10 is inserted through the tissue 24.

Reference sequentially to FIG. 4a and to FIG. 2 will show that when the loop 12 is formed, the edges 20 and 22 of the wound are thereby pulled into apposition. After cutting off the needle 14 and unnecessary parts of the one or more of the end portions 16 and 26 of the member 18, the remaining end segments 28 and 30 can be interlocked manually or with instruments thereby adding security to the wound closure. Alternatively, end segments 28 and 30 can be interlocked before the needle is removed.

A suture 10 which regains its undeformed shape at an elevated temperature may also be advantageously constrained using a stiff sleeve 32 as illustrated in FIG. 3. The stiff sleeve 32 prevents the shape memory change from occurring prematurely if the temperature increases at some time during storage or during heat sterilization. When the suture 10 is to be used, it can be immersed in a cold medium or it can be refrigerated with the sleeve 32 in place. The sleeve can thus be removed just before the suture 10 is placed into the tissue 24. Alternatively, the sleeve 32 can be used to directly drive the needle 14 through the tissues 24. The sleeve 32 may act as a heat sink to keep the suture relatively cool and delay the shape memory change from occurring. This can allow more time for placement of the deformed suture into the tissue. The sleeve 32 can also have a sharpened distal end and can be used to push the member 18 through the tissue 24. Generally, the needle 14 should be held by the sleeve 32 in such an instance so that relative rotation is prevented and so that the longitudinal axis of the needle 14 where it is connected to the first end portion 16 of the member 18 does not flex significantly relative to the longitudinal axis of the sleeve 32. Once the needle 14 has been driven appropriately through the tissue 24, the suture 10 can be advanced further with the help of an instrument such as a conventional needle holder (not shown) and the sleeve 32 can simply be slipped off of the second end portion 26 of the member 18.

Once the suture 10 has assumed the shape shown in FIG. 4a, the needle 14, and generally part of the first end portion 16 of the suture 10, are cut off or removed and the remaining portion of the suture 10 is warmed (by body heat and/or by applied heat). The remaining suture ends 28 and 30 can be interlocked as shown in FIG. 2. Alternatively, needle 14 and part of the first end portion 16 can be removed after interlocking the end segments 28 and 30.

The embodiment of FIG. 4a shows the second end portion 26 of the member 18 having a bulge or prominence 33 which is larger in cross section than is the cross section of the needle 14. The prominence 33 acts as a stop at the surface 34 of the tissue 24 as the suture 10 is pulled through the tissue 24 by the needle 14. The prominence 33 will abut the tissue surface 34 and will not readily pass through it. Alternatively, and as shown in FIG. 4b, the suture 10 may have a sharp bend 36 in its second end portion 26 which functions in the same manner as does the prominence 33 of FIG. 4a. In the embodiments of FIGS. 4a and 4b the end portions 16 and 26 of the member 18 can be cut off to form end segments 28 and 30 which can be interlocked as shown in FIG. 2.

FIGS. 5-8 disclose other embodiments of a suture 10 which rely on SMAs, whether they convert from their deformed shape to their undeformed shape pseudoelastically on release of stress or on heating. In FIGS. 5-8 the needle 14 has already been removed and the excess parts of the first end portion 16 and of the second end portion 26 of the member 18 have likewise been removed. In each of these Figures, the portion of the Figure labeled "A" illustrates the shape of the suture 10 as it has been placed into the tissue 24 but before the pseudoelastic effect or heating have caused the suture 10 to resume its undeformed shape. The diagrams labelled "B" illustrate alternate shapes of the suture 10 after the pseudoelastic or heating conversion of the suture 10 to its undeformed shape have occurred.

FIG. 5 illustrates, in the portion labeled B1, the situation where the SMA acts to reduce the radius of curvature of at least a portion of the suture 10 such that the tissue edges 20 and 22 are drawn and/or held together. In the embodiment of FIG. 5, portion B1, the end segments 28 and 30 bend sharply and curl inwardly generally toward the wound. In the embodiment of FIG. 5 shown in B2, the end segments 28 and 30 bend sharply and curl outwardly generally away from the wound. The end segments 28 and 30 may or may not contact or actually penetrate the tissue surface 34. The end segments 28 and 30 need not bend in the general plane of the main portion of the suture 10 and the ends 28 and 30 may each even bend to opposite sides of the general plane of the main portion of the suture 10. Indeed, in some cases, it may be desirable to have the end segments 28 and 30 bend in planes which are perpendicular to the general plane of the main portion of the suture 10.

FIG. 6 illustrates, in portions B1 and B2 thereof, two further embodiments of a suture 10 which utilizes a SMA. The SMA in the embodiment of FIG. 6 tends to reduce the radius of curvature of at least a portion of the suture 10 such that the tissue edges 20 and 22 are drawn and/or held together. The end segments 28 and 30 bend even more and curl inwardly generally more towards the wound, as shown in portion B1 of FIG. 6, or they bend even more and curl outwardly and generally away from the wound even more as shown in portion B2 of FIG. 6, as compared to the FIG. 5 embodiment. In these embodiments of the suture 10, the end segments 28 and 30 intentionally curl enough so that their respective tips 38 and 40 do not contact or penetrate the tissue surface 34. This serves to minimize irritation of the tissue surface 34 by the tips 38 and 40 of the end segments 28 and 30. As with the embodiments of FIG. 5, the end segments 28 and 30 need not bend in the general plane of the main portion of the suture 10.

FIG. 7 illustrates three additional embodiments of a suture 10 which utilize a SMA. The SMA acts to reduce the radius of curvature of at least a portion of the suture 10 so that the tissue edges 20 and 22 are drawn and/or held together as with other embodiments of the invention. However, the end portions 16 and 26 cross each other so that the respective tip 38, 40 of each end portion 16, 26 reaches the opposite side of the wound. In the embodiment illustrated in portion B1 of FIG. 7, the end portions 16 and 26 bend so that their tips 38, 40 contact or penetrate the tissue surface 34. In the embodiment illustrated in portion B2 of FIG. 7, end segments 28 and 30 of end portions 16 and 26 bend even more sharply than the rest of the suture 10 and curl generally inward towards the wound so that the respective tips 38 and 40 of the end segments 28 and 30 do not contact or penetrate the tissue surface 34. Again, this feature minimizes tissue irritation. In the embodiment of portion B3 of FIG. 7, the end segments 28 and 30 curl away from the tissue surface 34 so that the tips 38 and 40 do not contact or penetrate the tissue surface 34. As with the other embodiments discussed, the end segments 28 and 30 can bend in any desired plane.

FIG. 8 illustrates a suture 10 which is placed across the wound in more than a single throw. In particular, FIG. 8 illustrates a suture 10 which is placed across the wound in two throws. However, the suture 10 can be designed for any number of throws resulting in, if desired, what is known as a "running suture." Once the suture 10 is in position, its end segments 28 and 30 can assume any of the configurations illustrated for other embodiments of the invention. Alternatively, a prominence 33 as in FIG. 4a, or a sharp bend 36 as shown in FIG. 4b, can be present. In this embodiment, as in the other embodiments discussed, the conversion of the SMA from its less austenitic state towards its more austenitic state acts to reduce the radius of curvature of at least a portion of the suture 10 so that tissue edges 20 and 22 are drawn and/or held together. Portion A of FIG. 8 shows the suture 10 in position but the wound edges 20 and 22 not yet drawn together, while portion B shows an embodiment of the suture 10 in its predominantly austenitic undeformed configuration. In all of the embodiments shown, the suture 10 can be designed so that it can be placed deeply through the entire thickness of each tissue edge 20, 22. In this manner the tissue edges 20, 22 can be drawn and/or held together utilizing a single layer of sutures 10.

In accordance with the method of the invention, the tissues edges 20, 22 of a wound are sutured by inserting the member 18, while it is in its deformed longitudinally extending shape through the tissue 24 adjacent the tissue edges 20, 22 which define the wound and in the position for the member 18 to assume its undeformed suturing loop 12 shape.

The member 18 is subjected to conditions which cause it to recover towards its undeformed suturing loop form 12 whereby it draws and holds the tissue edges 20, 22 of the wound together.

The conditions to which the member 18 is subjected may comprise raising the temperature of the alloy to the temperature of the patient or to a higher temperature, thereby causing the suture 10 to leave its deformed shape and assume its undeformed shape. When temperature is used to convert the suture 10 from its deformed shape to its undeformed shape, the suture 10 may be placed in its deformed shape by cooling it to a temperature at which it can be so shaped and will retain its deformed shape, and then applying sufficient stress to cause it to assume the desired deformed shape.

An alternative set of conditions to which the suture 10 may be subjected to cause it to convert from its deformed shape to its undeformed suturing loop form 12 is by releasing stress on the member 18 sufficiently to allow a martensitic-to-austenitic phase change along with a concomitant change in shape. In such an instance, the suture 10 is generally put in its deformed shape by, at ambient temperature, being held under stress. This deformed shape can be maintained during insertion of the suture 10 through the tissue 24 due to the resistance of the tissue 24 and until the suture 10 is in position across the wound. As the stress is released, the suture 10 then assumes its loop form.

Industrial Applicability

The present invention provides sutures 10 for drawing and/or holding tissue edges 20, 22 of wounds together.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A suture for suturing a wound in the tissue of a patient defined by tissue edges comprising a member, formed of an alloy, which member has a first end portion, a second end portion and a first undeformed shape and which is deformable into a second deformed shape, said member having the property of recovering towards the first shape on being subjected to specified conditions; and the first shape being that of a suturing loop adapted to draw and hold the tissue edges defining the wound together and the second shape being adapted to allow said first end of said member to be drawn through said tissue in a position such that on recovery of the member towards the first shape the tissue edges are urged together.

2. A suture as set forth in claim 1, wherein said second shape is longitudinally extending.

3. A suture as set forth in claim 2, wherein said member in its second shape has the property of recovering substantially to the first shape on being subjected to said specified conditions.

4. A suture as set forth in claim 2, wherein said alloy contains martensitic phase when said member is in said second shape and wherein the austenitic phase content of the alloy when said member is in said first shape is greater than the austenitic phase content of the alloy when the member is in the second shape and wherein said specified conditions comprise releasing stress on said member sufficiently to allow some martensitic to austenitic phase change.

5. A suture as set forth in claim 4, wherein said loop shape is generally circular.

6. A suture as set forth in claim 2, wherein said loop shape is generally circular.

7. A suture as set forth in claim 1, wherein said alloy is predominantly martensitic when said member is in said second shape and is predominantly austenitic when said member is in said first shape and wherein said specified conditions comprise raising the temperature of at least a portion of said member to at least the temperature of the patient.

8. A suture as set forth in claim 7, wherein said second end portion of said member is formed into a hook adapted to engage with said first end portion of said member when said member is in its first shape.

9. A suture as set forth in claim 7, wherein said second end portion of said member is formed into a hook adapted to engage with the first end portion of the member after the member has recovered towards its first shape thereby holding the edges of the wound together.

10. A suture as set forth in claim 7, wherein said loop shape is generally circular.

11. A suture as set forth in claim 1, wherein said first end portion of said member is formed into a needle adapted to pierce tissue.

12. A suture as set forth in claim 1, further including:
a tissue piercing needle attached to extend longitudinally from said first end portion of said member.

13. A suture as set forth in claim 1, wherein said second end portion of said member is formed into a hook adapted to engage with said first end portion of said member after said member has recovered towards its first loop shape holding the edges of the wound together.

14. A suture as set forth in claim 1, wherein said first and second end portions of said member have respective exposed ends and said member has a final shape such that said first and second end portions curl so that the exposed ends do not touch the patient after the suture has been drawn through the tissue edges defining the wound and the member has recovered toward its first shape.

15. A suture as set forth in claim 1, wherein said first and second end portions of said member have respective exposed ends and said member has a final shape such that said exposed ends touch the patient after the suture has been drawn through the tissue edges defining the wound and the member has recovered toward its first shape.

16. A suture as set forth in claim 1, wherein said first and second end portions of said member have respective exposed ends and said first shape is such that said first and second end portions curl across the wound and into contact with the tissue across the wound after the suture has been drawn through the tissue edges defining the wound and the member has recovered toward its first shape.

17. A suture as set forth in claim 16, wherein said first shape is such that said exposed ends do not contact the tissue after the suture has been drawn through the tissue edges defining the wound and the member has recovered toward its first shape.

18. A suture as set forth in claim 1, wherein said second end portion of said member includes means for retarding said second end portion from being drawn through the tissue.

19. A suture as set forth in claim 18, wherein said retarding means comprises an enlarged sized portion, in transverse cross-section, of said second end portion of said member.

20. A suture as set forth in claim 18, wherein said retarding means comprises a bend in said second end portion of said member.

21. A suture as set forth in claim 1, further including:
a sleeve about at least a portion of said member when said member is in its second shape and being adapted so that said member is maintained in its second shape.

22. A suture as set forth in claim 21, wherein the sleeve holds at least a portion of the member in its second shape.

23. A suture as set forth in claim 21, wherein the sleeve has a sharpened piercing end adapted to pierce the tissue to position the member in position to hold the tissue edges of the wound together.

24. A suture as set forth in claim 21, wherein said first end portion of said member is formed into a needle and extends from the sleeve.

25. A suture as set forth in claim 21, further including:
a tissue piercing needle attached to extend longitudinally from said first end portion of said member, said needle extending from said sleeve.

26. A method of suturing a wound in the tissue of a patient defined by tissue edges, comprising:
inserting a member having a first undeformed suturing loop shape and a second deformed shape, said member being in its second shape, through the tissue adjacent the tissue edges defining the wound into position for the member to recover towards its first suturing loop shape; and
subjecting said member to conditions which cause it to recover towards its first suturing loop form whereby it draws and holds the tissue edges of the wound together.

27. A method as set forth in claim 26, further including, after member has so recovered:
interlocking first and second end portions of said member.

28. A method as set forth in claim 26, wherein said member is formulated of an alloy which is predominantly martensitic when said member is in said second shape and is predominantly austenitic when said member is in said first shape and wherein said subjecting step comprises raising the temperature of at least a portion of said member to a temperature which induces martensitic to austenitic phase change.

29. A method as set forth in claim 28, further including prior to said inserting step:
cooling said member to a temperature at which it can be shaped into its second shape; and
shaping said member into its second shape.

30. A method as set forth in claim 26, wherein said member is formulated of an alloy which contains martensitic phase when said member is in said second shape under stress and wherein the austenitic phase content of the alloy when said member is in said first shape is greater than second shape and wherein said subjecting step comprises releasing stress on said member sufficiently to allow sufficient martensitic to austenitic phase change to cause said member to recover towards its first shape.

31. A method as set forth in claim 26, further including, prior to said inserting step:
attaching a needle to a first end portion of said member.

32. A method as set forth in claim 31, further including prior to or after the member has recovered towards its first suturing loop shape:
removing the needle from the first end portion of the member.

33. A method as set forth in claim 26, further including, prior to said inserting:
positioning a sleeve about at least a portion of said member; and, either prior to or following said inserting,
removing said sleeve from about said member.

34. A method of suturing a wound in the tissue of a patient defined by tissue edges, comprising:
providing a member having a first undeformed suturing loop shape and a second deformed shape, said member being in its second shape
inserting the member through the tissue adjacent the tissue edges defining the wound into position for the member to recover towards its first suturing loop shape; and
subjecting said member to conditions which cause it to recover towards its first suturing loop form whereby it draws and holds the tissue edges of the wound together.

35. A method as set forth in claim 34, further including, after the member has so recovered:
interlocking first and second end portions of said member.

36. A method as set forth in claim 34, wherein said member comprises an alloy which is predominantly martensitic when said member is in said second shape and is predominantly austenitic when said member is in said first shape and wherein said subjecting step comprises raising the temperature of at least a portion of said member to at least the temperature of the patient.

37. A method as set forth in claim 36, further including, prior to said inserting step:
cooling said member to a temperature at which it can be shaped into its second shape; and shaping said member into its second shape.

38. A method as set forth in claim 34, wherein:
(1) the member comprises an alloy which contains martensitic phase when said member is in said second shape;
(2) the austenitic phase content of the alloy when said member is in said first shape is greater than the austenitic phase content of the alloy when said member is in said second shape; and
(3) the subjecting step comprises releasing stress sufficiently to allow some martensitic to austenitic phase change.

39. A method as set forth in claim 34, further including, prior to said inserting step:
attaching a needle to a first end portion of said member.

40. A method as set forth in claim 39, further including prior to or after the member has recovered towards its first suturing loop shape:
removing the needle from the first end portion of the member.

41. A method as set forth in claim 34, further including, prior to said inserting:
positioning a sleeve about at least a portion of said member; and, either prior to or following said inserting,
removing said sleeve from about said member.

42. A method of suturing a wound in the tissue of a patient defined by tissue edges, comprising:
a member which has a first undeformed suturing loop shape into a second deformed shape;
inserting the member through the tissue adjacent the tissue edges defining the wound into position such that the member can recover towards tis first suturing loop shape; and
subjecting said member to conditions which cause it to recover towards its first suturing loop form whereby it draws and holds the tissue edges of the wound together.

43. A method as set forth in claim 42, further including, after the member has so recovered:
interlocking first and second end portions of said member.

44. A method as set forth in claim 42, wherein said member comprises an alloy which is predominantly martensitic when said member is in said second shape and is predominantly austenitic when said member is in said first shape and wherein said subjecting step comprises raising the temperature of at least a portion of said member to at least the temperature of the patient.

45. A method as set forth in claim 44, further including, prior to said inserting step:
cooling said member to a temperature at which it can be shaped into its second shape; and
shaping said member into its second shape.

46. A method as set forth in claim 42, wherein:
(1) the member comprises an alloy which contains martensitic phase when said member is in said second shape;
(2) the austenitic phase content of the alloy when said member is in said first shape is greater than the austenitic phase content of the alloy when said member is in said second shape; and
(3) the subjecting step comprises releasing stress sufficiently to allow some martensitic to austenitic phase change.

47. A method as set forth in claim 42, further including, prior to said inserting step:
attaching a needle to a first end portion of said member.

48. A method as set forth in claim 47, further including prior to or after the member has recovered towards its first suturing loop shape:
removing the needle from the first end portion of the member.

49. A method as set forth in claim 42, further including, prior to said inserting:
positioning a sleeve about at least a portion of said member; and, either prior to or following said inserting,
removing said sleeve from about said member.

* * * * *